US00PP12910P2

(12) United States Plant Patent
Wu et al.

(10) Patent No.: US PP12,910 P2
(45) Date of Patent: Sep. 3, 2002

(54) BUFFALOGRASS PLANT NAMED 'UCD-95'

(75) Inventors: Lin L. Wu, Davis; Victor A. Gibeault, Riverside, both of CA (US)

(73) Assignee: The Regents of the University of California, Oakland, CA (US)

( * ) Notice: Subject to any disclaimer, the term of this patent is extended or adjusted under 35 U.S.C. 154(b) by 81 days.

(21) Appl. No.: 09/866,689

(22) Filed: May 30, 2001

(51) Int. Cl.[7] ..... A01H 5/00
(52) U.S. Cl. ..... Plt./391
(58) Field of Search ..... Plt./391

*Primary Examiner*—Bruce R. Campell
*Assistant Examiner*—Annette H. Para
(74) *Attorney, Agent, or Firm*—Burns, Doane, Swecker & Mathis, L.L.P.

(57) ABSTRACT

A new female diploid cultivar of Buffalograss (i.e., *Buchloe dactyloides*) is provided that resulted from mass selection. Superior turf quality is displayed over the entire growing season. The stolons are of fine texture and the internodes are short. Good drought tolerance is displayed. The plant exhibits superior turf green color retention and short winter dormany. The growth habit is extremely competitive with respect to weeds. A high turf density is made possible with a rapid stolon spreading rate and short plant height that provides an attractive low maintenance turf.

2 Drawing Sheets

BACKGROUND OF THE INVENTION

Buffalograss, *Buchloe dactyloides* (Nutt) Engelm., is recognized to be a warm-season stoloniferous, sod-forming, perennial grass. It is a drought tolerant and an important range grass found mainly in the central prairies of the United States with its full range of distribution extending from Canada to Mexico (U.S. Agriculture Handbook, 1959). The buffalograss is the only species of its genus. It contains diploid, tetraploid, and hexaploid races (Stebbins, 1975), of which only the latter occur in the Great Plains area.

The diploid race mainly occurs in Central Mexico and southern Texas (Reeder, 1971) and it has only recently been researched for economic values, especially for turfgrass development. Genetic variation in shade, cold, and salinity tolerance has been detected among buffalograss germplasm collections (Wu and Lin, 1994, 1996; Wu and Harivandi, 1995). Allelochemical compounds found in buffalograss function as a broad-spectrum preemergence herbicide. Accordingly, they are potentially useful traits for buffalograss breeding (Wu et al., 1997).

SUMMARY OF THE INVENTON

The new cultivar of the present invention is a vegetatively propagated, drought resistant female buffalograss clone resulting from mass selection. Seeds of diploid buffalograss germplasms were collected from locations in Mexico including San Jose, San Clayetano, and Venegas. The population sizes of the three population were 215 from San Jose, 250 from San Clayetano and 300 from Venegas. Plants were established from the seeds and these were space planted during 1987 in an experimental field at the University of California, located at Davis, Calif., U.S.A. The plants were mowed on a weekly basis at a two-inch height during the growing season from May to the end of October.

Individual clones were selected for rapid vegetative growth, high turf density, and extended winter turf green coloration. Approximately 80 percent of the plants were eliminated during this selection for the above characteristics. The remaining plants were subjected to drought stress by terminating irrigation during the following summer months for a period of eight weeks from June 15$^{th}$ to August 18$^{th}$. Two male plants and two female plants were selected from each of the three populations on the basis of their superior performance. The six male and six female clones were grown close together in the field to achieve mass crossing and the resulting seeds were harvested from the female plants. These seeds were germinated in the greenhouse and grown for six weeks before being transplanted into the field. Approximately six hundred plants were space planted in the field and were subjected to turfgrass management. More specifically, the plants were mowed weekly to a height of 2 inches, were irrigated every 10 days, and in April and in August one pound of nitrogen was applied per 1000 square feet as ammonium sulfate. Two clones from this planting previously were selected and were released. These were the 'Hilite 15' cultivar (U.S. Plant Pat. No. 8,896) and the 'Hilite 25' cultivar (U.S. Plant Pat. No. 8,897). The new cultivar of the present invention additionally was studied and evaluated and was selected and carefully preserved as a result of its exhibited combination of characteristics.

It was found that the new diploid female buffalograss cultivar of the present invention exhibits:

(a) stolons of fine texture,
(b) superior drought tolerance,
(c) a competitive growth habit,
(d) short winter dormancy
(e) superior turf green color retention, and
(f ) high turf density with a rapid stolon spreading rate and short plant height that provides a low maintenance quality turf.

The new cultivar of the present invention can be readily distinguished from the 'Hilite 15' and 'Hilite 25' cultivars by shorter and thinner internodes, fewer burrs per spikelet, smaller burrs, and fewer flowers per burr. As reported hereafter, under field management conditions at Davis and Riverside, Calif., U.S.A., a superior turf quality was displayed over the entire growing season by the new cultivar of the present invention. Also, a greater vegetative spreading rate, a higher turf density, greater injury regrowth potential, greater shade tolerance, and better turf green color retention in the fall have been displayed by the new cultivar. A greater dry weight allocation in the vegetative growth and a lesser weight allocation in the sexual reproductive parts have been displayed by the new cultivar.

The new cultivar of the present invention has been vegetatively propagated by the use of stolons, sprigs, and plugs. Such asexual propagation was carried out initially in greenhouses at the Department of Environmental Horticulture, University of California, located at Davis, Calif., U.S.A. Thereafter vegetative propagation has been carried out at Riverside, and near Anaheim, Calif., U.S.A. Such propagation has confirmed that the characteristics of the new cultivar are stable and are reliably transmitted to subsequent generations.

The new cultivar of the present invention has been named 'UCD-95'.

BRIEF DESCRIPTION OF THE PHOTOGRAPHS

The accompanying photographs show typical specimens of the 'UCD-95' cultivar as depicted in color as nearly true as it is possible to make the same in color illustrations of this character. The plants were grown at Davis, Calif., U.S.A.

DETAILED DESCRIPTON

Figure 1:
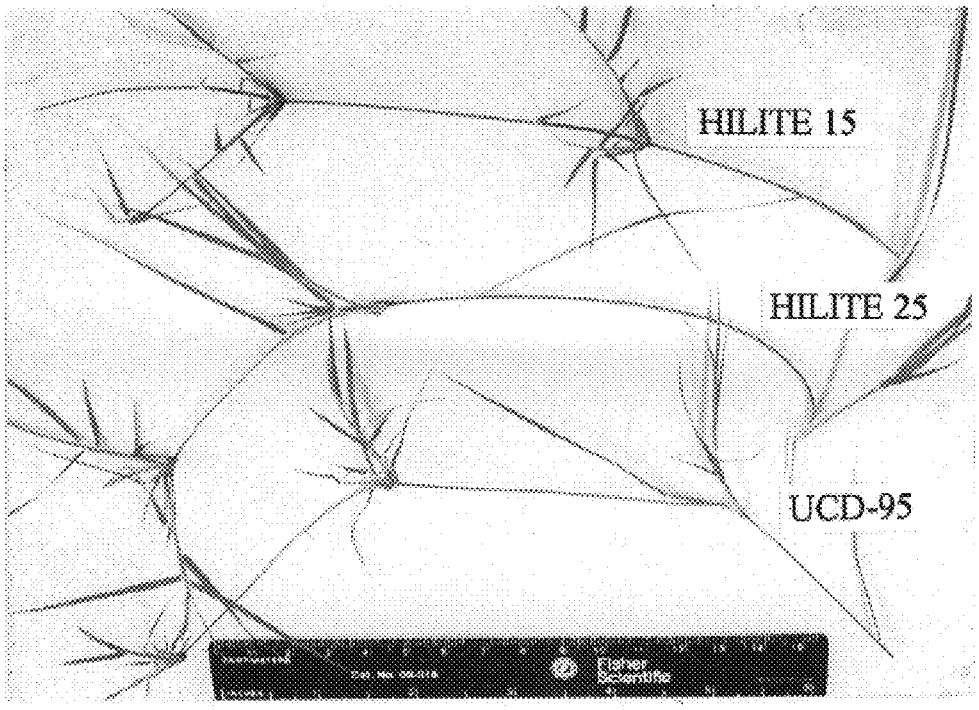
FIG. 1 shows for comparative purposes representative stolons of the new cultivar and that of the 'Hilite 15' and 'Hilite 25' cultivars wherein the shorter stolon diameter and shorter internode length of the new cultivar are displayed.
Figure 2:
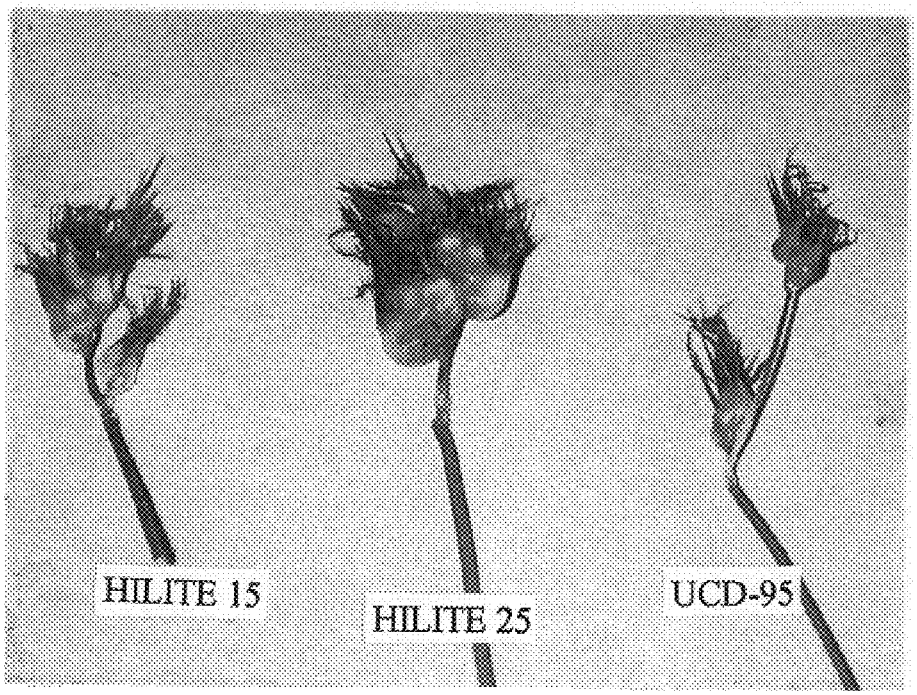
FIG. 2 shows typical sexual reproductive parts of the new cultivar as well as those of the 'Hilite 15' and 'Hilite 25' cultivars for comparative purposes. Smaller and fewer burrs per inflorescence are displayed by the new cultivar of the present invention.
Figure 3:
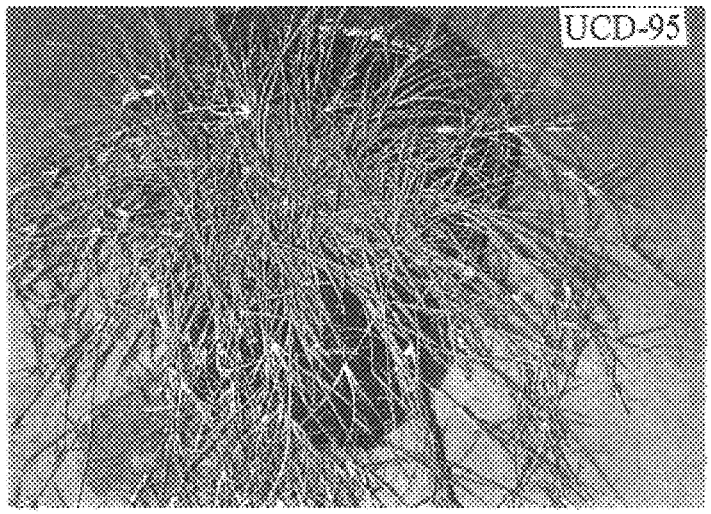
FIG. 3 shows a typical container grown plant of the new cultivar during the summer.
Figure 4:
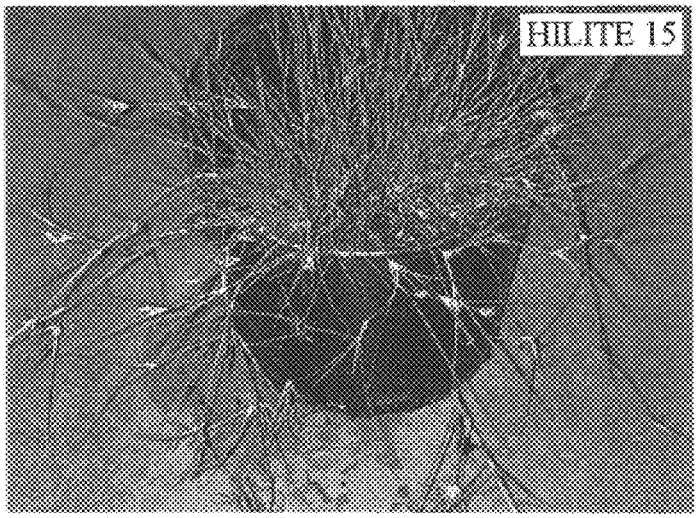
FIG. 4 shows for comparative purposes a typical container grown plant of the 'Hilite 15' cultivar during the summer.
Figure 5:
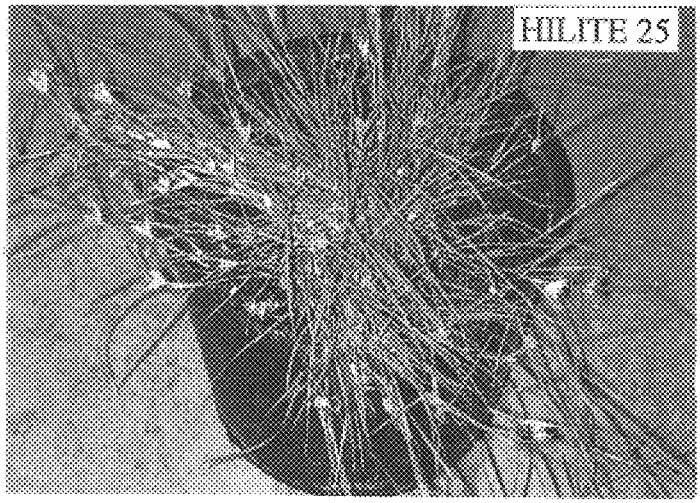
FIG. 5 shows for comparative purposes a typical container grown plant of the 'Hilite 25' cultivar during the summer.

Reference to color is based upon the Inter-Society Color Council-National Bureau of Standards Color Chart (September 1988).

The new cultivar of the present invention is particularly adaptable to areas of the California central valley and southern California, the transition zone of the United States, and from Central Mexico to the southern portion of the Great Plains of the United States. Its growth is best in direct sunlight with temperatures above 20° C. Its performance under shaded conditions is comparable to bermudagrasses.

The new cultivar may be established by planting sod, springs, or plugs. Planting two-inch plugs on 12 inch centers establishes a solid turf coverage within 10 weeks (from June to August). It is a female plant which is a vegetatively propagated clone and spreads by stolonization. 'UCD-95' does not produce male inflorescences as appear in seeded buffalograss. Nor does it produce viable seed in the absence of pollination. It forms a dense, uniform, fine-textured, stoloniferous, deep green turf. In the absence of mowing 'UCD-95' reaches height of approximately 10 to 15 cm. It requires minimal water, nutrition, and other maintenance. 'UCD-95' displays dense and aggressive growth characteristics that render it highly competitive against unwanted weeds. In 'UCD-95', aesthetic attributes of density, uniformity, and appealing turf color combine with durability, competitiveness and low maintenance requirements. Together, these agronomic attributes render 'UCD-95' particularly suitable for home lawns, recreational turf areas such as the fairway and rough of golf courses, industrial parks, and ground cover along roadsides. 'UCD-95' is further characterized in the following information and Tables as observed in greenhouses and experimental fields of the University of California at Davis, Calif., U.S.A., except where otherwise indicated.

The leaf color of 'UCD-95' is deep green (118 deep YG) when undergoing active growth and changes to yellow (73. p.OY) when dormant.

The 'UCD-95' Cultivar

Origin: A single superior diploid female buffalograss plant selected from mass crosses of three diploid buffalograss germplasms collected from central Mexico. Plants used for the description were approximatively 10 years old.

Classification:

*Botanical.*—*Buchloe dactyloides* (Nutt.) Engelm.

*Chromosome number.*—2n=20.

*Form.*—Monocot Gramineae.

*Growth habit.*—A stoloniferous vegetatively reproducing female plant with short vertical growth and a rapid horizontal growth rate. Its fibrous root system knits in most media within three weeks from plugs or stolon cuttings. In season, it produces dense, uniform, fine-textured turf and holds its green color to near the freezing temperature during the winter months.

Establishment rate:

*Sod.*—1 to 2 weeks.

*Plugs.*—6 to 8 weeks (in July and August).

*Springs.*—6 to 8 weeks.

*Regions of adaptation.*—From central Mexico to the central Great Plains of the United States and is particularly adaptable to areas of the California Central Valley and southern California.

*Blade.*—Shape. — Long, slender, with pointed leaf tip.

*Length.*—Approximately 8 cm on average.

*Width.*—Approximately 1.2 mm on average.

*Hairiness.*—Absent, is glabrous.

*Mature plant height.*—10 to 15 cm.

Internode:

*Length.*—Approximately 57.6 mm on average of 2nd internode from the tip of ten stolons of greenhouse grown plants, and less than that of the 'Hilite 15' and 'Hilite 25' cultivars.

*Diameter.*—Approximately 0.64 mm on average of 2nd internode from the tip of ten stolons of greenhouse grown plants, and less than that of the 'Hilite 15' and 'Hilite 25' cultivars.

*Node pigmentation.*—Purple (259.d.p R).

*Stolon color.*—Green (120.m.YG).

Leaf color:

*Active.*—Deep green (118. deep YG).

*Dormant.*—Yellow (73.p.OY).

*Soils.*—Heavy clay, silty clay, loam, calcareous, neutral to alkaline.

Inflorescence:

*Male.*—Absent.

In the Tables that follow, characteristics of the 'UCD-95' cultivar of the present invention are compared to those diploid buffalograss cultivars 'Hilite 15' (U.S. Plant Pat. No. 8,896) and 'Hilite 25' (U.S. Plant Pat. No. 8,897), and to the well-known hexaploid buffalograss 'Texoka' cultivar (non-patented in the United States). In the Tables, "P" designates "present" and "A" designates "absent".

TABLE 1

| Morphological Comparison | 'UCD-95' | 'Hilite 25' | 'Hilite 15' | 'Texoka' |
|---|---|---|---|---|
| A. Vegetative Traits | | | | |
| 1. STOLONS | P | P | P | P |
| a. Color and pigmentation | Green (120.m. YG) | Green (120.m. YG) | Green (120.m. YG) | Green (262.gy. pR) |
| b. Internode length (mm) (mean value of 2nd internode from the tip of 10 stolons of greenhouse grown plants) | 57.6c* | 70.1b | 59.5c | 95.0a |
| c. Internode diameter (mm) (mean value of the 2nd internode from the tip of 10 stolons of greenhouse grown plants) | 0.64c | 0.71b | 0.76b | 0.90a |
| 2. NODES | | | | |
| a. Color and pigmentation | purple (259.d.pR) | purple (262.gY. pR) | purple (259.d.pR) | purple (259.d. p.R) |
| 3. RHIZOMES | A | A | A | A |
| 4. LEAF BLADE | | | | |
| a. Color | | | | |
| (1) Active | deep green (118.deep YG) | deep green (118.deep YG) | deep green (118.deep YG) | blue green (164.m. bG) |
| (2) Dormant | Yellow (73.p.OY) | Yellow 73.p.OY) | Yellow (73.p.OY) | Yellow (164. mbG) |
| b. Dimensions (flag leaf) | | | | |
| (1) Width (mm) (mean value of 10 samples of fully extended leaves on 2nd internode of each stolon) | 1.2b | 1.2b | 1.2b | 2.0a |
| (2) Length (cm) | 8b | 8b | 8b | 13.0a |
| c. Hairs | | | | |
| (1) Abaxial | A | A | A | P |
| (2) Adaxial | A | A | A | P |
| 5. SHEATH (adaxial margin) | | | | |
| a. Hairs | A | A | A | P |
| b. Length (cm) | 1.8b | 1.8b | 1.5b | 2.1a |
| 6. COLLAR | | | | |
| (1) Hairness | P | P | P | P |
| B. Floral Traits | | | | |
| 1. MALE INFLORESCENCE | A | A | A | P |
| 2. FEMALE INFLORESCENCE | P | P | P | P |
| a. Stigma color | purple | purple | purple | purple |
| b. Spikelet | | | | |
| (1) Number of burrs (mean of 10 spikelets) | 2.6c | 4.5a | 3.8b | 4.5a |
| (2) Burr length (mm) | 3.2c | 4.4b | 4.0b | 6.5a |
| (3) Burr width (mm) | 2.7b | 4.2b | 4.4b | 6.2a |

TABLE 1-continued

| Morphological Comparison | 'UCD-95' | 'Hilite 25' | 'Hilite 15' | 'Texoka' |
|---|---|---|---|---|
| (4) # Flowers per burr (mean of 10 flowers) | 2.4a | 2.5a | 2.5a | 2.5a |
| 7. Chromosome number (2n) | 20 | 20 | 20 | 60 |

*Means separated by Duncan's new multiple range test, P = 1%

It is apparent from the above data that the new cultivar of the present invention displays shorter internodes and thinner stolons than the comparative cultivars. Also, 'UCD-95' exhibits a lesser number of burrs per spikelet, smaller burrs, and a lesser number of flowers per burr.

TABLE 2

Turfgrass Overall Quality Rating of 'UCD-95' in Comparison to Two Other Diploid Buffalograss Varieties and the Old Hexaploid Buffalograss Cultivar 'Texoka' Over the Growing Season of 1995 Under Field Management Conditions.
Turfgrass quality ratings 1 to 9 where 9 is ideal turf

| | MAY | JUNE | JULY | AUG. | SEPT. | NOV. | MEAN |
|---|---|---|---|---|---|---|---|
| 'UCD-95' | 9a* | 9a | 9a | 9a | 9a | 9a | 9.0a |
| 'Hilite 25' | 6b | 7b | 7b | 7b | 7b | 7b | 6.8b |
| 'Hilite 15' | 6b | 7b | 7b | 7b | 7b | 7b | 6.8b |
| 'Texoka' | 3c | 5c | 5c | 5c | 4c | 1c | 1.0c |

*Means separated by Duncan's new multiple range test, P = 1%.

The turfgrass quality is based on uniformity, density of stand, texture of turf canopy, smoothness of surface, and growth habit (Beard J. B., Turfgrass Science, 1973). The field trials were conducted at Davis in northern California and at Riverside in southern California, U.S.A. Superior turf quality was consistently displayed by the new 'UCD-95' cultivar of the present invention under field growing conditions.

TABLE 3

Performance of 'UCD-95' in Comparison to Two Other Diploid Cultivars and the Old Hexaploid Cultivar 'Texoka' for Specific Characteristics.

| Character (1 to 9 scale where 9 is best) | 'UCD-95' | 'Hilite 25' | 'Hilite 15' | 'Texoka' |
|---|---|---|---|---|
| Rate of vegetative spread | 9a* | 7b | 7b | 4c |
| Turf density | 9a | 9b | 9b | 7c |
| Injury regrowth potential | 9a | 7b | 7b | 4c |
| Shade tolerance | 9a | 7b | 7b | 3c |
| Genetic color | 9a | 9b | 9b | 6c |
| Fall turf green color retation | 9a | 7b | 7b | 4c |
| Heat tolerance | 9a | 9a | 9a | 9a |
| Drought tolerance | 9a | 9a | 9a | 9a |
| Salinity tolerance | 8a | 8a | 9a | 8b |

*Means separated by Duncan's new multiple range test, P = 1%.

It will be noted that 'UCD-95' was superior or equal to the other cultivars for all characteristics identified in Table 3 except salinity tolerance where it was exceeded only by the 'Hilite 15' cultivar. The fall turf green retention characteristic and the rate of vegetative growth for the new cultivar were particularly superior when compared to the other cultivars.

TABLE 4

Dry Weight Allocation in Above Ground Reproductive and Vegetative Plant Parts As Percent of Total.

| Dry Weight (Percent) | 'UCD-95' | 'Hilite 25' | 'Hilite 15' | 'Texoka' |
|---|---|---|---|---|
| Reproductive Parts | | | | |
| Greenhouse grown without cutting back | 22c* | 53a | 41b | 55a |
| Field grown under 5 cm mowing height | 52b | 62a | 60a | 58a |
| Vegetative Parts | | | | |
| Greenhouse grown without cutting back | 78a | 47c | 59b | 45c |
| Field grown under 5 cm mowing height | 48a | 38b | 40b | 42b |

*Means separated by Duncan's new multiple range test, P = 1%.

The dry weight allocation measurement was conducted in August of 1997 during the peak season for the development of sexual reproductive parts. It will be noted that a greater dry weight allocation in the vegetative growth and a lesser dry weight allocation in the reproductive parts is displayed by the new cultivar of the present invention when compared to the previously released cultivars.

TABLE 5

Comparative Weed Competitiveness Study Ratings on Scale of 1 to 9 Where 9 Equals "No Weeds" and 1 Equals "Complete Weed Cover".

| Buffalograss Cultivars | January | March | June | July | Mean |
|---|---|---|---|---|---|
| 'UCD-95' | 9 | 9 | 9 | 9 | 9.0a* |
| 'Bonnie Bare' | 4 | 5 | 6 | 5 | 5.0f |
| '378' | 7 | 6 | 5 | 5 | 5.7f |
| '92-118' | 9 | 8 | 9 | 9 | 8.7a |
| 'Midget' | 9 | 8 | 8 | 7 | 8.2b |
| '609' | 9 | 8 | 8 | 8 | 8.2b |
| 'Cody' | 6 | 6 | 4 | 6 | 5.5f |
| 'Texoka' | 6 | 7 | 8 | 6 | 6.7e |
| 'Bam-1000' | 7 | 8 | 7 | 7 | 7.2d |
| 'Bison' | 5 | 3 | 4 | 4 | 4.0g |
| 'Stampede' | 9 | 9 | 9 | 8 | 8.7a |
| 'Tatanka' | 6 | 7 | 9 | 9 | 7.7c |
| '86-120' | 5 | 2 | 6 | 4 | 4.2g |
| '86-61' | 4 | 2 | 5 | 4 | 3.7g |

*Means separated by Duncan's new multiple range test, P = 1%.

The weed study was conducted in year 2000 in the field at a southern location of Riverside, Calif., U.S.A., when plants were mowed to a height of 7.5 cm. The weeds were predominantly dichondra, oxalis, dandelion, and annual bluegrass. The superior weed competitiveness of the new cultivar of the present invention was displayed. Weeds could not compete well with the new cultivar at any time during the growing season.

References Cited

Stebbins, G. L., (1975) "The Role of Polyploid Complexes in the Evolution of North American Grasslands", *Taxon*, 24(1):91 to 106.

Reeder, Jr., (1971) "Notes on Mexican Grasses IX Miscellaneous Chromosome Numbers-3", *Brittonia,* 23:107 to 117.

Wu, L., and A., Harivandi, (1995) "Buffalograss Response to Cold, Shade, and Salinity" *California Turfgrass Culture,* 45:7 to 10.

Wu, L., and H. Lin, (1994) Salt tolerance and salt uptake in diploid and polyploid buffalograss (*Buchloe dactyloides*). *J. Plant Nutr.,*17: 1905 to 1928.

Lin, H., and L. Wu, (1996) "Effects of Salt Stress on Root Plasma Membrane Characteristics of Salt-Tolerant and Salt-Sensitive Buffalograss Clones" *Environmental and Experimental Botany,* 36:239 to 254.

Wu, L., Xun Guo, and Ali Harivandi (1997) "Allelopathic Effects of Phenolic Acods in Buffalograss (*Buchloe dactyloides*) clippings on Growth of Annual Bluegrass (*Poa annua*) and Buffalograss Seedlings" *Environmental and Experimental Botany,* 39:159 to 167.

We claim:

1. A new and distinct cultivar of *Bachloe dactyloides* plant having the following combination of characteristics:

(a) stolons of fine texture,
(b) superior drought tolerance,
(c) a competitive growth habit,
(d) short winter dormancy,
(e) superior turf green color retention, and
(f) high turf density with a rapid stolon spreading rate and short plant height that provides a low maintenance turf;

substantially as illustrated and described.

* * * * *